US008367071B2

(12) United States Patent
Green

(10) Patent No.: US 8,367,071 B2
(45) Date of Patent: Feb. 5, 2013

(54) VEROTOXIN B SUBUNIT FOR IMMUNIZATION

(75) Inventor: Allan M. Green, Cambridge, MA (US)

(73) Assignees: Inserm-Transfert, Paris (FR); Universite Pierre et Marie Curie (UPMC), Paris Cedex (FR)

(*) Notice: Subject to any disclaimer, the term of this patent is extended or adjusted under 35 U.S.C. 154(b) by 626 days.

(21) Appl. No.: 10/368,314

(22) Filed: Feb. 13, 2003

(65) Prior Publication Data
US 2004/0013681 A1    Jan. 22, 2004

Related U.S. Application Data

(63) Continuation of application No. 09/312,338, filed on May 14, 1999, now abandoned.

(60) Provisional application No. 60/085,693, filed on May 15, 1998.

(51) Int. Cl.
*A61K 39/395* (2006.01)
(52) U.S. Cl. .................................. 424/193.1; 424/185.1
(58) Field of Classification Search ... 514/2; 424/184.1, 424/194.1, 197.11; 530/350
See application file for complete search history.

(56) References Cited

U.S. PATENT DOCUMENTS

| | | | |
|---|---|---|---|
| 5,198,344 A | 3/1993 | Croop et al. | |
| 5,338,839 A | 8/1994 | McKay et al. | |
| 5,350,890 A | 9/1994 | Fairbrother et al. | |
| 5,747,028 A * | 5/1998 | Calderwood et al. | 424/93.2 |
| 5,980,898 A * | 11/1999 | Glenn et al. | 424/184.1 |
| 6,613,882 B1 * | 9/2003 | Goud et al. | 530/350 |

FOREIGN PATENT DOCUMENTS

| | | |
|---|---|---|
| EP | 130132 A1 | 1/1985 |
| EP | 439 954 A2 | 8/1991 |
| EP | 439 954 A3 | 8/1991 |
| EP | 532090 A2 | 3/1993 |
| EP | 739984 A1 | 10/1996 |
| WO | WO 91/09871 A1 | 7/1991 |
| WO | WO 93/16186 A1 | 8/1993 |
| WO | WO 93/17115 A2 | 9/1993 |
| WO | WO 95/14085 | 5/1995 |
| WO | WO 96/16178 A1 | 5/1996 |
| WO | WO 97/13410 A1 | 4/1997 |
| WO | WO 98/11229 A2 | 3/1998 |
| WO | WO 98/22140 A2 | 5/1998 |

OTHER PUBLICATIONS

Stedman's medical dictionary, 25th ed, 1990, p. 1652-1653.*
Vadolas J et al, 1995, Eur J immunol, 25(4): 969-75.*
Di Tommaso A et al, 1996, Infection and Immunity, 64(3): 974-9.*
Hirschowitz, E A et al, Jul. 1998, Gene therapy, 5(7): 975-83.*
Apostolopoulos V et al, 1995, Cancer letters, 90: 21-26.*
Kupcu S et al, 1996, J Immunol methods, 196(1): 73-84.*
White et al, 1968, 4th ed, Principles of Biochemistry, McGraw-Hill book Co., New York, pp. 153-154.*
Sandvig, K et al, 1994, J Cell Biol,126: 5364.*
Johannes L et al, JBC, 1997, 272(31): 19554-19561.*
Hui N et al, 1997, Mol Biol Cell, 8(9): 1777-1787.*
White et al, 1968, 4th ed, Principles of Biochemistry, McGraw-Hill book Co, New York, p. 151.*
Restifo et al, 1994, Folia Biologica (Praha) 40: 74-88.*
Domenech et al, 1995, J Immunol, 155: 4766-4774.*
Johannes et al, 1996, J Mol Biol Cell, 7 (Suppl), p. 75A, abstract # 433.*
Haigh et al (Oncology, (Nov. 1999) 13 (11) 1561-74).*
Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Porgador et al J. Immunol. vol. 158 p. 834 (1997).*
Allinquant et al. "Downregulation of Amyloid Precursor Protein Inhibits Neurite Outgrowth In Vitro," J. Cell Biol. 128(5):919-27 (1995).
Boël et al. "*BAGE*: a New Gene Encoding an Antigen Recognized on Human Melanomas by Cytolytic T Lymphocytes," Immunite 2:167-75 (1995).
Bower et al. "Cloning and Characterization of the *Bacillus subtilis* birA Gene Encoding a Repressor of the Biotin Operon," J. Bacteriology 177(9):2572-75 (1995).
Brichard et al. "The Tyrosinase Gene Codes for an Antigen Recognized by Autologous Cytolytic T Lymphocytes on HLA-A2 Melanomas," J. Exp. Med. 178:489-95 (1993).
Calderwood et al. "Nucleotide sequence of the Shiga-like toxin genes of *Escherichia coli*," Proc. Natl. Acad. Sci. USA 84(13):4364-68 (1987).
Chicz et al. "Analysis of MHC-presented peptides: applications in autoimmunity and vaccine development," Immunol. Today 15(4):155-60 (1994).
Ciernik et al. "Mutant Oncopeptide Immunization Induced CTL Specifically Lysing Tumor Cells Endogenously Expressing the Corresponding Intact Mutant p53," Hybridoma 14(2):139-42 (1995).
Coulie at al. "A New Gene Coding for a Differentiation Antigen Recognized by Auto-logous Cytolytic T Lymphocytes on HLA-A2 Melanomas," J Exp Med 180:35-42 (1994).
Davis et al. "DNA-Mediated Immunization in Mice Induces a Potent MHC Class I-Restricted Cytotoxic T Lymphocyte Response to the Hepatitis B Envelope Protein," Hum. Gene Therapy 6:1447-56 (1995).
De Plaen et al. "Structure, chromosomal localization, and expression of 12 genes of the MAGE family," Immunogenetics 40:360-69 (1994).
Feltkamp et al. "Vaccination with cytotoxic T lymphocyte epitope-containing peptide protects against a tumor induced by human papillomavirus type 16-transformed cells," Eur. J. Immunol. 23:2242-49 (1993).

(Continued)

*Primary Examiner* — Sheela J Huff
(74) *Attorney, Agent, or Firm* — Venable LLP; Nancy J. Axelrod; Michael A. Gollin

(57) ABSTRACT

Methods for stimulating an immune response in a mammal by administering a toxin-antigen conjugate are provided. Pharmaceutical compositions and methods for treating an antigen-related state are also described.

21 Claims, 6 Drawing Sheets

OTHER PUBLICATIONS

Furukawa et al. "Clonal Expansion of CD8+ Cytotoxic T Lymphocytes against Human T Cell Lymphotrophic Virus Type I (HTLV-I) Genome Products in HTLV-I-asso-ciated Myelopathy/Tropical Spastic Paraparesis Patients," J Clin Invest 94:1830-39 (1994).

Gnjatic et al. "Mapping and ranking of potential cytotoxic T epitopes in the p53 protein: effect of mutations and polymorphism on peptide binding to purified and refolded HLA molecules," Eur. J. Immunol. 25:1638-42 (1995).

Head et al. "Preparation of VT1 and VT2 hybrid toxins from their purified dissociated subunits. Evidence for B subunit modulation of a subunit function," J Biol Chem. 266(6):3617-21 (1991).

Johannes et al. "Shiga toxin as a tool to study retrograde transport," Molec Biol Cell 7(Supp):75a (1996).

Johannes et al. "Retrograde Transport of KDEL-bearing B-fragment of Shiga Toxin," J. Biol. Chem. 272:19554-61 (1997).

Kawakami et al. "Identification of the Immunodominant Peptides of the MART-1 Human Melanoma Antigen Recognized by the Majority of HLA-A2-restricted Tumor Infiltrating Lymphocytes," J. Exp. Med. 180:347-52 (1994).

Kim et al. "Dynamic Measurement of the pH of the Golgi Complex in Living Cells Using Retrograde Transport of the Verotoxin Receptor," J. Cell Biol. 134(6):1387-99 (1996).

Lamb, "Nucleotide sequence of cloned cDN coding for preproricin," Eur. J. of Biochem. 148(2):265-70 (1995).

Lee et al. "Major histocompatibility complex class I presentation of exogenous soluble tumor antigen fused to the B-fragment of Shiga toxin," Eur. J. Immunol. 28:2726-37 (1998).

Lewis et al. "A human homologue of the yeast HDEL receptor," Nature 348:162-63 (1990).

Lewis et al. "Ligand-Induced Redistribution of a Human KDEL Receptor from the Golgi Complex to the Endoplasmic Reticulum," Cell 68:353-64 (1992).

Lingwood, "Verotoxins and Their Glycolipid Recetpros," Adv. Lipid Res. 25:189-211 (1993).

Murray et al. "Identification of Target Antigens for the Human Cytotoxic T Cell Response to Epstein-Barr Virus (EBV): Implications for the Immune Control of EBV-positive Malignancies," J. Exp. Med. 176:157-68 (1992).

O'Brien et al. "Shiga Toxin: Biochemistry, Genetics, Mode of Action, and Role in Pathogenesis," Curr. Top. Microbiol. Immunol. 180:65-94 (1992).

Peace et al. "Induction of T Cells Specific for the Mutated Segment of Oncogenic P21$^{ras}$ protein by Immunization In Vivo with the Oncogenic Protein," J. Immunotherapy 14(2):110-14 (1993).

Pelham et al. "Toxin entry: how reversible is the secretory pathway?" Trends Cell Biol. 2:183-85 (1992).

Rapak et al. "Retrograde transport of mutant ricin to the endoplasmic reticulum with subsequent translocation to the cytosol," Proc. Natl. Acad. Sci. USA 94:3783-3788 (1997).

Rehermann et al. "The Cytotoxic T Lymphocyte Response to Multiple Hepatitis B Virus Polymerase Epitopes During and After Acute Viral Hepatitis" J Exp Med 181:1047-58 (1995).

Sandvig et al. "Retrograde Transport from the Golgi complex to the ER of Both Shiga Toxin and the Nontoxic Shiga B-gragment is Regulated by Butryric Acid and cAMP," J. Cell. Biol. 126(1):53-64 (1994).

Sandvig et al. "Retrograde transport of endocytosed Shiga toxin to the endolasmic reticulum," Nature 358:510-12 (1992).

Seidah et al. "Complete Amino Acid Sequence of *Shigella* Toxin B-chain," J. Biol. Chem. 261(30):13928-31 (1986).

Strockbine et al. "Cloning and Sequencing of the Genes for Shiga Toxin from *Shigella dysenteriae* Type 1," J. Bacteriology 170(3):1116-22 (1988).

Su et al. "Construction of Stable LamB-Shiga Toxin B Subunit Hybrids: Analysis of Expression in *Salmonella typhimurium* aroA Strains and Stimulation of B Subunit-Spe-cific Mucosal and Serum Antibody Responses," Infection and Immunity 60:3345-59 (1992).

Traversari et al. "A Nonapeptide Encoded by Human Gene MAGE-1 is Recognized on HLA-A1 by Cytolytic T Lymphocytes Directed against Tumor Antigen MZ2-E," J. Exp. Med. 176:1453-57 (1992).

Tsao et at "A Versatile plasmid expression vector for the production of biotinylated pro-teins by site-specific, enzymatic modification in *Escherichia coli*," Gene 169:59-64 (1996).

Van den Eynde et al. "A New Family of Genes Coding for an Antigen Recognized by Autologous Cytoloic T Lymphocutes on a Human Melanoma," J. Exp. Med. 182:689-98 (1995).

Austyn JM. "New insights into the mobilization and phagocytic activity of dendritic cells."*J Exp Med.* Apr. 1, 1996;183(4):1287-92.

Bos JD. "The skin as an organ of immunity."*Clin Exp Immunol.* Jan. 1997;107 Suppl 1:3-5.

van der Bruggen P, et al. "A gene encoding an antigen recognized by cytolytic T lymphocytes on a human melanoma." Science. Dec. 13, 1991;254(5038):1643-7.

van der Bruggen P, et al. "A peptide encoded by human gene MAGE-3 and presented by HLA-A2 induces cytolytic T lymphocytes that recognize tumor cells expressing MAGE-3." *Eur J Immunol.* Dec. 1994;24(12):3038-43.

Cella M, et al. "Origin, maturation and antigen presenting function of dendritic cells" *Curr Opin Immunol.* Feb. 1997;9(1):10-6. Review.

Edelman R. "Vaccine adjuvants". *Rev Infect Dis.* May-Jun. 1980;2(3):370-83.

Feltkamp MC, et al. "Cytotoxic T lymphocytes raised against a subdominant epitope offered as a synthetic peptide eradicate human papillomavirus type 16-induced tumors." *Eur J Immunol.* Sep. 1995;25(9):2638-42.

Florenes VA, et al. "Expression of the neuroectodermal intermediate filament nestin in human melanomas." *Cancer Res.* Jan. 15, 1994;54(2):354-6.

Gao XM, et al. "Recombinant *Salmonella typhimurium* strains that invade nonphagocytic cells are resistant to recognition by antigen-specific cytotoxic T lymphocytes." *Infect Immun.* Sep. 1992;60(9):3780-9.

Glenn, G.M. et al. "Skin immunization made possible by cholera toxin" *Nature* 391(6670):851 (Feb. 26, 1998).

Heemels MT, et al. "Generation, translocation, and presentation of MHC class I-restricted peptides".*Annu Rev Biochem.* 1995;64:463-91.

Huang AY, et al. "Role of bone marrow-derived cells in presenting MHC class I-restricted tumor antigens". *Science.* May 13, 1994;264(5161):961-5.

Kavanaugh DY, et al. "Immunologic dysfunction in cancer." *Hematol Oncol Clin North Am.* Aug. 1996;10(4):927-51.

Ke Y, et al. "Ovalbumin injected with complete Freund's adjuvant stimulates cytolytic responses." *Eur J Immunol.* Feb. 1995;25(2):549-53.

Kovacsovics-Bankowski M, et al. "Efficient major histocompatibility complex class I presentation of exogenous antigen upon phagocytosis by macrophages".*Proc Natl Acad Sci U S A.* Jun. 1, 1993;90(11):4942-6.

Kurts C, et al. "Constitutive class I-restricted exogenous presentation of self antigens in vivo" *J Exp Med.* Sep. 1, 1996;184(3):923-30.

Lipford GB, et al. "CpG-containing synthetic oligonucleotides promote B and cytotoxic T cell responses to protein antigen: a new class of vaccine adjuvants." *Eur J Immunol.* Sep. 1997;27(9):2340-4.

Matousek MP, et al. "Distinct effects of recombinant cholera toxin B subunit and holotoxin on different stages of class II MHC antigen processing and presentation by macrophages." *J Immunol.* Jun. 1, 1996;156(11):4137-45.

Monaco JJ. "A molecular model of MHC class-I-restricted antigen processing." *Immunol Today.* May 1992;13(5):173-9.

Moore MW, et al. "Introduction of soluble protein into the class I pathway of antigen processing and presentation. Cell". Sep. 9, 1988;54(6):777-85.

Nair S, et al. "Soluble proteins delivered to dendritic cells via pH-sensitive liposomes induce primary cytotoxic T lymphocyte responses in vitro." *J Exp Med.* Feb. 1, 1992;175(2):609-12.

Nestle FO, et al. "Vaccination of melanoma patients with peptide- or tumor lysate-pulsed dendritic cells." *Nat Med.* Mar. 1998,4(3):328-32.

Pan ZK, et al. "Regression of established tumors in mice mediated by the oral administration of a recombinant *Listeria monocytogenes* vaccine" *Cancer Res.* Nov. 1, 1995;55(21):4776-9.

Perez F, et al. "Antennapedia homeobox as a signal for the cellular internalization and nuclear addressing of a small exogenous peptide" *J Cell Sci.* Aug. 1992;102 ( Pt 4):717-22.

Pieters J. "MHC class II restricted antigen presentation."*Curr Opin Immunol.* Feb. 1997;9(1):89-96.

Pudymaitis A, et al. "Susceptibility to verotoxin as a function of the cell cycle."*J Cell Physiol.* Mar. 1992;150(3):632-9.

Reis e Sousa C, et al. "Major histocompatibility complex class I presentation of peptides derived from soluble exogenous antigen by a subset of cells engaged in phagocytosis." *J Exp Med.* Sep. 1, 1995;182(3):841-51.

Redfield RR, et al. "Disseminated vaccinia in a military recruit with human immunodeficiency virus (HIV) disease". *N. Engl J Med.* Mar. 12, 1987;316(11):673-6.

Rock KL. "A new foreign policy: MHC class I molecules monitor the outside world" *Immunol Today.* Mar. 1996;17(3):131-7.

Rosenberg SA, et al. "Treatment of patients with metastatic melanoma with autologous tumor-infiltrating lymphocytes and interleukin 2". *J Natl Cancer Inst.* Aug. 3, 1994;86(15):1159-66.

Sabzevari H, et al. "Human cytotoxic T-cells suppress the growth of spontaneous melanoma metastases in SCID/hu mice." *Cancer Res.* Oct. 15, 1993;53(20):4933-7.

Sallusto F, et al. "Efficient presentation of soluble antigen by cultured human dendritic cells is maintained by granulocyte/macrophage colony-stimulating factor plus interleukin 4 and downregulated by tumor necrosis factor α" *J Exp Med.* Apr. 1, 1994;179(4):1109-18.

Schutze-Redelmeier MP, et al. "Introduction of exogenous antigens into the MHC class I processing and presentation pathway by *Drosophila antennapedia* homeodomain primes cytotoxic T cells in vivo". *J Immunol.* Jul. 15, 1996;157(2):650-5.

Smigel K. "Women flock to ABMT for breast cancer without final proof." *J Natl Cancer Inst.* Jul. 5, 1995;87(13):952-5.

Snider DP. "The mucosal adjuvant activities of ADP-ribosylating bacterial enterotoxins." *Crit Rev Immunol.* 1995;15(3-4):317-48. Review.

Steinman RM."The dendritic cell system and its role in immunogenicity." *Annu Rev Immunol.* 1991;9:271-96.

Stevenson PG, et al. "Protection against influenza virus encephalitis by adoptive lymphocyte transfer". *Virology.* May 26, 1997;232(1):158-66.

Traversari C, et al. "Transfection and expression of a gene coding for a human melanoma antigen recognized by autologous cytolytic T lymphocytes." *Immunogenetics.* 1992;35(3):145-52.

Watts C. "Capture and processing of exogenous antigens for presentation on MHC molecules". *Annu Rev Immunol.* 1997;15:821-50.

Milita P. Matousek et al.,; "Distinct Effects of Recombinant Cholera Toxin B Subunit and Holotaxin on Different Stages of Class II MHC Antigen Processing and Presentation by Macrophages", The Journal of Immunology, 1996, 156: pp. 4137-4145.

Frank O. Nestle et al.,: "Vaccination of melanoma patients with peptide- or tumor lysate-pulsed dendritic cells", Nature Medicine, vol. 4, No. 3, Mar. 1998 pp. 328-332.

L. Johannes et al., "Study of Shiga Toxin B-Fragment Retrograde Transport: Development of Intracellular Targeting Tools with Potential Applications in Cancer Therapy," Meeting of the French Society of Cell Biology, Mar. 8-10, 1998, Institut Curie, Paris, France. (Abstract).

G. M. Glenn et al., "Skin immunization made possible by cholera toxin," Nature, vol. 351, Feb. 26, 1998, p. 851.

B.D. Tzschaschel et al., "Towards a vaccine candidate against *Shigella dysenteriae* 1: expression of the Shiga toxin B-subunit in an attenuated *Shigella flexnero* aroD carrier strain," Microbial Pathogenesis 1996; vol. 21, pp. 277-288.

\* cited by examiner

_US 8,367,071 B2_

VEROTOXIN B SUBUNIT FOR IMMUNIZATION

RELATED APPLICATIONS

This application is a continuation application of application Ser. No. 09/312,338, filed on May 14, 1999 (CPA filed Jan. 14, 2002), now abandoned, which in turn claims priority to provisional application No. 60/085,693, filed May 15, 1998. The contents of all of the aforementioned applications are hereby incorporated by reference.

BACKGROUND OF THE INVENTION

Dendritic cells are sentinels of the immune system. They originate from a bone marrow progenitor, travel through the blood and are seeded into non-lymphoid tissue, e.g., skin. Dendritic cells capture and process exogenous antigens for presentation as peptide-MHC complexes at the cell surface and then migrate via the blood and afferent lymph to secondary lymph nodes. In the lymph nodes, they interact with T-lymphocytes to facilitate activation of helper and killer T cells (Steinman, R. (1991) _Annu. Rev. Immunol._ 9:271; Celia et al. (1997) _Curr. Opin. Immunol._ 9:10).

Dendritic have been named according to their appearance and distribution in the body. For example, dendritic cells located in the epidermis are known as Langerhans cells. Dendritic cells located in the dermis and interstitium are known as interstitial dendritic cells. Blood, veiled, and lymphoid dendritic cells are found, respectively, in the circulatory system, afferent lymph and the lymph nodes. Dendritic cells have further been characterized by lineage, by maturation stage, by functional and phenotypic characteristics of these stages, and by mechanisms involved in their migration and function (Cella et al., supra; Austyn, J. (1996) _J. Exp. Med._ 183:1287).

Recent work has demonstrated that cholera toxin can act as a potent transcutaneous adjuvant in noninvasive, transcutaneous immunization in mice (Glenn, G. M. et al. _Nature_(1998) 391: 851). Cholera toxin applied to the surface of the skin stimulates a strong immune response to coadministered antigens such as diphtheria or tetanus toxoids. This method is particularly important given the large skin surface area and the existence of potent immune cells within it (see, e.g., Bos, J. D., _Clin. Exp. Immunol.,_ 107 (Suppl. 1), 3-5, 1997).

Studies with cholera toxin suggest that the holotoxin enhances the presentation of soluble peptides on macrophages, however it inhibited intracellular processing of soluble or bacterial antigens. In contrast, the recombinant B subunit enhanced surface presentation of the antigens, but did not inhibit intracellular processing (Matousek, M. P., J. G. Nedrud and C. V. Harding, _J. Immunol.,_ 156, 4137-4145, 1996). Animal studies have also demonstrated the potent capacity of dendritic cells to induce anti-tumor immunity (Nestle, F. O. et al. _Nature Medicine,_ 4:328-332, 1998).

SUMMARY OF THE INVENTION

In one embodiment, the present invention pertains to a method for stimulating an immune response in a mammal, by administering to the mammal a toxin-antigen conjugate such that an immune response in the mammal is stimulated. Preferably, the toxin-antigen conjugate is administered to the mammal transcutaneously through the skin or a mucous membrane.

In an advantageous embodiment, the toxin-antigen conjugate includes, for example, a tumor antigen, a viral antigen, or a bacterial antigen. The tumor antigen may be derived from lung tissue, skin tissue, breast tissue, stomach tissue, colon tissue, rectal tissue or brain tissue. In one preferred embodiment, the tumor antigen is from, for example, a melanoma tumor. Advantageously, the toxin-antigen conjugate of the invention may include a toxin such as a shiga toxin, a verotoxin, or a cholera B toxin. Preferably, the toxin is the B fragment of verotoxin.

In another embodiment, the invention features a method for treating an antigen-related state in a mammal, by administering to the mammal an effective amount of an antigen-toxin conjugate and stimulating an immune response in the mammal. Preferably, the toxin-antigen conjugate is administered to the mammal transcutaneously through the skin or a mucous membrane, e.g., a mucous membrane located in the mammal's respiratory tract, gastrointestinal tract or reproductive tract. In a particularly preferred embodiment, the mammal is a human. Advantageously, an adjuvant may also be administered with the conjugate of the invention.

The invention also pertains to a pharmaceutical composition comprising a toxin-antigen conjugate and a pharmaceutically acceptable carrier. Preferably, the composition is suitable for administration to the mammal transcutaneously through the skin or a mucous membrane. Advantageously, the pharmaceutically acceptable carrier is suitable for administration orally, transdermally, or intrabronchially. Preferably, the pharmaceutical composition is suitable for non-invasive administration.

The present invention relates to recombinant proteins such as toxin-antigen conjugates which comprise a receptor-binding non-toxic fragment of a toxin, e.g., a Shiga toxin or a verotoxin B subunit, and an epitope of a tumor antigen, e.g., Mage 1. The invention also features methods for using the claimed conjugates. The toxin-antigen conjugates can be used, for example, to stimulate an immune response in a mammal, or for treating an antigen-related state in a mammal. The toxin-antigen conjugates can also be used for presenting antigens on antigen-presenting cells and for the formulation of pharmaceutical compositions.

DETAILED DESCRIPTION OF THE INVENTION

Figure 1:
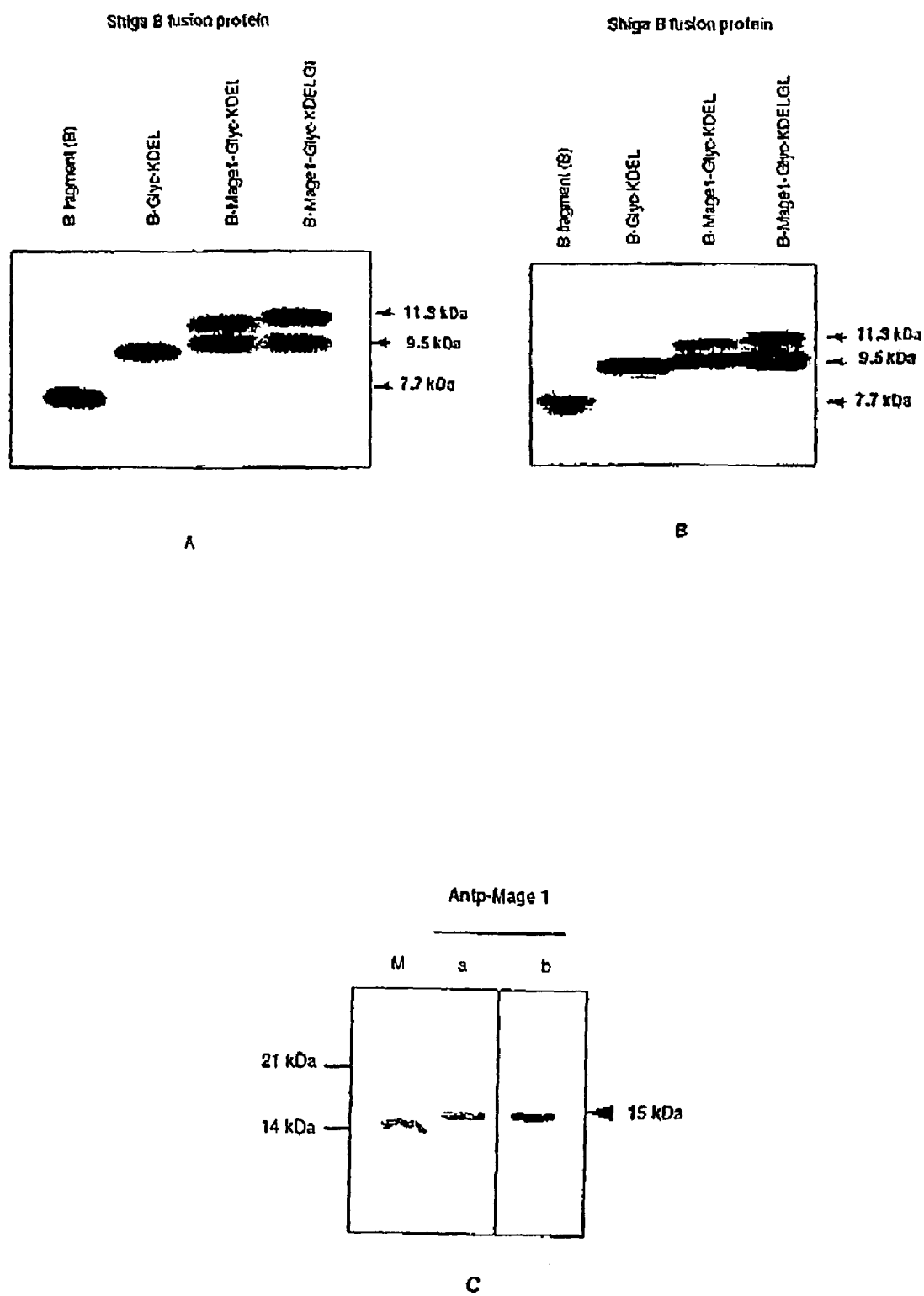
FIG. 1: Biochemical characterization of Shiga B-Mage 1 and Ant-Mage 1 fusion proteins. The B-fragment of Shiga toxin (=B) or recombinant B-Glyc-KDEL, B-Mage1-Glyc-KDEL, or B-Mage1-Glyc-KDELGL proteins were analyzed by electrophoresis on Tris-tricine gels under reducing conditions. The gels were then stained with Coomassie blue (A) or revealed by Western blot analysis with the monoclonal antibody 13C4 directed against the B-fragment of Shiga toxin (B). Antennapedia-Mage 1 (Antp-Mage 1, C) fusion protein was analyzed by Coomassie blue staining (a) or Western blot analysis with anti-His Tag antibody (b).

The present invention pertains, at least in part, to pharmaceutical compositions and methods for stimulating an immune response. The invention features a recombinant protein, e.g., a toxin-antigen conjugate, comprising an antigen or an antigen epitope, e.g., Mage 1, which is associated, e.g., by covalent linkage, to a toxin, e.g., a Shiga, toxin, a verotoxin B. In a preferred embodiment, the pharmaceutical compositions are suitable for transcutaneous administration either through the skin or a mucous membrane, e.g., of the respiratory system, gastrointestinal system or the reproductive system.

The term "antigen" includes agents which provoke an immune response independently and those which are provoke an immune response when incorporated in to a conjugate of the invention. The term "antigen epitope" includes fragments of proteins capable of determining antigenicity. An epitope may comprise, for example, a peptide of six to eight residues in length (Berzofsky, J. and I. Berkower, (1993) in Paul, W., Ed., *Fundamental Immunology*, Raven Press, N.Y., p.246). Some epitope may be significantly larger. The affinity of an antibody molecule for its cognate epitope ranges from low, e.g. $10^{-6}$ M, to high, e.g., $10^{-11}$ M.

For example, antigens include proteins and other molecules which are specifically associated with surfaces of particular types of cancer cells, e.g. tumor cells. Many forms of cancer can be characterized by production of proteins associated with that form of the disease, and are not found in normal tissue. Often these proteins are used at a specific stage of embryonic development, and are not observed during normal adult lifetime. These antigens are particularly useful as a source of epitopes for anti-cancer vaccines. Examples of tumor antigens that are envisioned as antigens for the conjugates of the present invention include those corresponding to cancers affecting the breast, ovarian, lung, skin, and brain. For example, breast tumors may be characterized by abnormally expressed receptors, e.g. those of the human-EGF-like receptor family (HER). Additionally, the¯ nestin¯ protein, which is expressed by neuroepithelial stem cells during normal mammalian fetal development, is also expressed on tumors of the central nervous system, including most forms of brain cancer (McKay, D. G. Ronald, U.S. Pat. No. 5,338,839, Aug. 16, 1994). It is also expressed on melanomas found on the skin and on those which have metastasized to other tissues (V. A. Florenes, R. Holm, O. Myklebost, U. Lendahl, O. Fodstad, 1994, *Cancer Res.* 54: 354-6). The present invention contemplates incorporating these antigens or epitopes of these antigens into compounds of the invention. Preferably, the antigens of the toxin-antigen conjugates of the invention are peptides associated with melanoma which may be derived, for example, recombinantly or from tumor cell lysate.

Other examples of tumors expressing antigens contemplated by the present invention include Wilm's tumor (A. J. Buckler, K. M. Call, T. M. Glaser, D. A. Haber, D. E. Housman, C. Y. Ito, J. Pelletier, Rose, E. A. Rose, U.S. Pat. No. 5,350,840), gastrointestinal cancer (R. Fishel et al, International Application WO 95/14085, 05/26/95), cancers characterized by development of multiple drug resistance during chemotherapy (J. M. Croop et al., U.S. Pat. No. 5,198,344), and cancers characterized by the presence of at least one of a large number of oncogenes well known to the skilled artisan, such as Rb, ras, and c-myc, the sequences of which are available for analysis to those with skill in the art.

Alternatively, antigens of the invention may be associated with the surfaces or secretion products of micro-organisms or pathogens. The term "pathogen" is meant to include organisms that cause disorders, such disorders produced by one or more particular species of bacteria, viruses, fungi, and protozoans which are disease-producing organisms. Examples of pathogens include gram-negative bacterial species such as *Escherichia coli* serotype 0157:H7, *Helicobacter pylori, H. mustelae, Haemophilus influenzae* and *H. ducreyi, Pseudomonas aeruginosa, Shigella dysenteria, Salmonella typhi* and *S. paratyphi*; Gram-positive bacterial species such as *Mycobacterium tuberculosis, M leprae, Clostridium tetani, Staphylococcus aureus*, and *Streptococcus hemolyticus*; obligate intracellular bacterial organisms such as Rickettsia and Chlamydia species; retroviruses, which are RNA containing viruses that use reverse transcriptase to synthesize complementary DNA, including but not limited to HIV-1, and -2; other pathogenic viruses such HSV-I and -II, non-A non-B non-C hepatitis virus, pox viruses, and rabies viruses; fungi such as Candida and Aspergillus species; protozoa such as *Cryptosporidium parvum, Entamoeba histolytica* and *Giardia lamblia*; and animal pathogens such as Newcastle disease virus. Obtaining unique epitopes from these organisms by screening proteins and by assaying peptides in vitro are commonly known to those skilled in the art; many examples have been described and the appropriate amino acid residue sequence may be accessed from Genbank.

The term "infection" is meant to include persistence and growth of a pathogen in a subject host. While symptoms used to diagnose the presence of infection include fever, inflammation, pain, joint and muscular sensations at or near sites of infection, the absence of one or more of these symptoms do not preclude infection in a subject host organism. The term "inflammation" indicates a set of host reactions that accompany infection, and may also be present in the absence of infection, for example, as a symptom of autoimmune reactions, degenerative diseases, tissue remodeling disorders, exposure to allergens, and/or other conditions. Inflammatory responses include cellular processes such as neutrophil, mast cell and basophil degranulation with associated release of proteases, histamines, and superoxide generation, and production of and responses to cytokines such as interferons and tumor necrosis factor.

One type of antigen can be an allergen. An "allergen" refers to a substance that can induce an allergic or asthmatic response in a susceptible subject. The number of allergens that elicit a sensitive response in a proportion of a population is enormous, and includes pollens, insect venoms, animal dander, dust mite proteins, fungal spores and drugs (e.g. penicillin). Examples of natural animal and plant allergens include proteins specific to the following genera: Felis (*Felis domesticus*); Canis (*Canis familiaris*); Dermatophagoides (e.g. *Dermatophagoides farinae*); Periplaneta (e.g. *Periplaneta americana*); Ambrosia (*Ambrosia artemiisfolia*; Lolium (e.g. *Lolium perenne* or *Lolium multiflorum*); Cryptomeria (*Cryptomeria japonica*); Alternaria (*Alternaria alternata*); Alnus (*Alnus gultinosa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattelia germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*); Thuya (e.g. *Thuya orientalis*), Chamaecyparis (e.g. *Chamaecyparis obtusa*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poa pratensis* or *Poa compressa*); Avena (e.g. *Avena sativa*); Holcus (e.g. *Holcus lanatus*); Anthoxanthum (e.g *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*). An "allergen associated state" includes states which are the resulting from an allergic or asthmatic response to an allergen.

The term "toxin" includes compounds which are capable of facilitating an immune response of the antigen. Exemplary toxins include cholera b chain, Shiga toxins, and preferably, shiga-like toxins, e.g., verotoxin. Shiga-toxin is a bacterial protein toxin of the $AB_5$ subunit family that is secreted by *Shigella dysenteriae*. The A-subunit inhibits protein biosynthesis in higher eukaryotic cells after transfer into the cytoplasm by modifying a conserved residue of 28S rRNA. The B-subunit, a homopentamer (%-B fragments) is responsible for toxin binding to and internalization into target cells by interacting with the glycolipid $Gb_3$ found in the plasma membrane of these cells. The B-fragment is not toxic but conserves the intracellular transport characteristics of the holotoxin which in many $Gb_3$ expressing cells is transported in a retrograde fashion from the plasma membrane via endosomes into the biosynthetic/secretory pathway.

In a related embodiment, the toxin is a Shiga-like toxin, e.g., verotoxin. Currently known verotoxins include verotoxin 1, verotoxin 2, verotoxin 2c and verotoxin 2e of subunit toxins elaborated by some strains of *E. coli*. These toxins are involved in the etiology of the hemolytic uremic syndrome and haemorrhagic colitis. Cell cytotoxicity is mediated via the binding of the B subunit of the holotoxin to the receptor glycolipid, globotriaosylceramide, in sensitive cells. Advantageously, the toxin of the invention is non-toxic, e.g., preferably, shiga-toxin B or verotoxin B.

The term "associated" includes covalent linkages between the toxin and the antigen. Preferred covalent linkages include, for example, peptide linkages and cyanogen bromide activation. The term also includes protein-protein interactions, hydrophobic interactions, Van der Waals interactions and ionic interactions. Examples include conjugates which comprise biotin.

In one embodiment, the toxin-antigen conjugate is produced recombinantly. Methods for producing compounds of the invention recombinantly are well known to the skilled artisan and are elaborated in the Example.

In a further embodiment, the toxin-antigen conjugate may further comprise an active or inactive endoplasmic reticulum retrieval signal. The term "endoplasmic reticulum retrieval signal" includes peptide sequences which enhance the ability of a conjugate of the invention to interact with cells involved in immune response. An example of an active endoplasmic reticulum retrieval signal is KDEL, which may, for example, advantageously be attached to the C-terminal of the toxin. An example of a suitable inactive endoplasmic reticulum retrieval signal is KDELGL. Advantageously, KDELGL is attached to the C-terminal of the toxin.

In a particularly preferred embodiment, the toxin-antigen conjugate of the invention, comprises verotoxin B and a tumor antigen, e.g., for example, a melanoma-associated peptide. Advantageously, the conjugate may be produced recombinantly.

The invention also features a method for stimulating an immune response in a mammal by administering to a mammal a toxin-antigen conjugate. Preferably, the stimulation of the immune response includes involvement of dendritic, e.g., Langerhans, cells. The term "immune response" includes any immunological response of the mammal to the conjugate of the invention. Advantageously, the immune response may include, for example, the promotion of T cells, generation of antibodies against the antigen, and/or the presentation of the antigen by dendritic cells, e.g. preferably, Langerhans cells. The term includes any response of the immunological system of the mammal to the conjugate of the invention. The term "stimulating" includes, for example, initiation or enhancement of an immune response.

Processing and presentation of antigens to T lymphocytes are critical events in the development of an immune response. As a general rule, Major histocompatibility Complex (MHC) class I molecules present endogenous peptide epitopes, mainly derived from cytosolic and nuclear proteins to CD8+ T lymphocytes (CTL) (Monaco, J. J. *Immunol. Today* (1992) 13: 173-179; Heemels, M. T. and Ploagh, H., *Annu. Rev. Biochem.* (1995) 64: 463491), whereas peptides derived from exogenous proteins are generated in the endocytic pathway and presented on MHC class II molecules to CD4. T lymphocytes (Janeway, C. A. Jr., et al., *Inf. Rev. Imunol.* (1993) 10:301-311; Pieters, J., *Curr. Opin, Immunol.* (1997) 9:89-96). However, different reports showed that self endogenous antigens expressed by normal or tumor tissues can be efficiently processed via an exogenous class I restricted pathway for presentation to CD8+ T cells.

In transgenic mice expressing a membrane bound form of ovalbumin (OVA) only in the pancreatic islet cells and in renal tubular cells, OVA derived peptides are presented in a class I restricted manner by cells from bone marrow origin in the draining lymph node of kidney or pancreas (Kurts, C., et al. *J Exp. Med*. (1996) 184:923-930). Huang et al. demonstrated that priming of T cells to MHC class I restricted tumor antigens required the transfer and processing of these antigens from tumor cells to bone marrow derived antigen presenting cells (Huang, A. Y., et al. *Science* (1994) 264: 961-965). In spite of these arguments demonstrating presentation in the context of MHC class I molecules and generation of CTL via an exogenous processing pathway, most studies failed to demonstrate efficient in vitro class I restricted presentation or induction of CTL in vivo with foreign exogenous soluble antigens (Moore, M. W., et al., *Cell* (1988) 54: 777-785; Rock, K, L., *Immunol. Today* (1996) 17: 131-137; Watts, C., *Annu. Rev. Immunol*. (1997)15:821-850).

Since CTL are an important component of the protective and therapeutic immune responses to viral infections and tumors (Sabzovari, H. et al. *Cancer. Res*. (1993) 53:4933-4937; Rosenburg, S. A., et al. *J Natl. Cancer. Inst*. (1994) 86:1159-1166; Stevenson. P. G., et al. *Virology* (1997) 232: 158-166; Feltkarnp, M. C. *Eur. J. Immunol*. (1995) 25:2638-2642), different strategies have been developed to allow MHC class I restricted presentation and stimulation of CTL by exogenous soluble antigens.

Recombinant live vectors such as Vaccinia, Listeria or Salmonella expressing viral or tumor antigens efficiently delivered these antigens to the cytosol, thereby allowing their introduction to the class I restricted presentation pathway and sensitization of CTL in vivo (Gao, X. M. et al. *Infect. Immunity* (1992) 60:3780-3789; Pan, Z. K. et al. *Cancer. Res*. (1995) 55:4776-4779; Tsang, K.Y. et al.,*J. Natl. Cancer. Inst*. (1995) 87:952-990). However, the use of like vectors poses risks for the recipient due to the potential pathogenicity of the vectors used, especially In immunosuppressed patients such as cancer and HIV infected subjects (Kavanaugh, D.Y. et al. *Hematol. Oncol. Clin. North. Arnenca* (1996) 10:927-951; Redfield, R. R. et al. *N. Eng. J. Med* (1987) 316:673-676).

Other approaches using particulate antigens linked to latex beads (Kovacsovics-Bankowski, M. et al., *Pro. Nat. Acad. Sci. USA* (1993) 90:4942-4946; Harding, C. V. et al. *J. Immmunol*. (1994) 153:4925-4933), fused with liposomes (Nair, S., et al., *J. Exp. Med*. (1992) 175:609-612) or associated with adjuvants (Ke, Y. et al. *Eur. J. Immunol*. (1995) 25:549-553; Lipford, G. B. et al. *Eur. J. Immunol*. (1997) 27:2340-2344) succeeded in introducing foreign antigen in the MHC class I pathway in vitro and in vivo. In most cases, phagocytosis was involved in this process and it appeared that this class I presentation pathway required high antigen concentrations and its efficiency was low (Reis e Sousa, C. et al. *J. Exp. Med* (1995) 1B2:841-851).

The term "mammal" includes warm blooded animals such as, for example, rodents (e.g. rats, mice, hamsters, squirrels), horses, cows, pigs, sheep, cats, dogs, bears, goats, and primates (e.g., monkeys, chimpanzees, gorillas, and, preferably, humans).

The term "dendritic cells" include Langerhans cells, interstitial dendritic cells, interdigitating dendritic cells, follicular dendritic cells and circulating dendritic cells. Langerhans cells are found in the epidermis and mucous membranes. Interstitial dendritic cells populate most organs such as the heart, lungs, liver, kidney, and gastrointestinal tract. Interdigiting dendritic cells are present in T-cell areas of the secondary lymphoid tissue and the thymic medulla. Circulating dendritic cells include "veiled cells" which constitute about 0.1% of the blood leukocytes.

In general, dendritic cells are covered with a maze of long membrane processes resembling dendrites of nerve cells. Due to their long dendritic processes, dendritic cells have been challenging to study using conventional procedures for isolating lymphocytes and accessory immune-system cells. Dendritic cells tend to express high levels of both class II MHC molecules and the co-stimulatory B7 molecule. For this reason, they are more potent antigen-presenting cells than macrophages and B cells, both of which need to be activated before they can function as APCs. After capturing an antigen in the tissues by phagocytosis or by endocytosis, dendritic cells migrate into the blood of lymph and circulate to various lymphoid organs where they present the antigen to T lymphocytes.

The invention also pertains to a method for treating an antigen-related state in a mammal by administering to the mammal a therapeutically effective amount of an antigen-toxin conjugate and, thereby, stimulating an immune response in the mammal. For example, this method includes coadministering an antigen with verotoxin B subunit or administering a antigen coupled to a verotoxin B subunit to a subject, e.g., a mammal, to stimulate the antigen presenting capabilities of dendritic cells.

The term "antigen-related state" includes micro-organism or pathogenic infections, allergen associated states, and, preferably, tumors such as, for example, breast, ovarian, brain, skin, lung, etc. Preferably, the antigen-related state is melanoma.

The term "treating" includes preventing and curing as well as ameliorating at least one symptom of the antigen-related state. It also includes the initiation of an immune response against an antigen-related state that the mammal may be susceptible to, but not necessarily suffering from. For example, in a mammal at risk for melanoma, a conjugate of the invention may be administered to said mammal, thus generating an immune response so as to prevent or delay the initiation of the potential melanoma.

The term "administering" includes routes of administration which allow the conjugate of the invention to perform its intended function, e.g. stimulate an immune response. Preferred routes of administration include, but are not limited to, orally, intrabronchially, and transdermally. Depending on the route of administration, the conjugate of the invention can be coated with or disposed in a selected material to protect it from natural conditions which may detrimentally effect its ability to perform its intended function. The conjugate of the invention can be administered alone or with a pharmaceutically acceptable carrier. Further, the conjugate of the invention can be administered as a mixture of conjugates of the invention, which also can be coadministered with a pharmaceutically acceptable carrier. The conjugate of the invention can be administered prior to the onset of an antigen-related state, or after the onset of an antigen-related state.

Preferably, the conjugates of the invention are administered to the mammal transcutaneously through the skin or through a mucous membrane. Mucous membranes include lubricated membranes of the inner linings of many internal systems of mammals. Examples of systems with mucous membranes include, but are not limited to, the respiratory system, the gastrointestinal tract and the reproductive tract. Preferred mucous membranes include, for example, the membranes of a mammals' nose, nasal passages, throat, lungs, mouth, stomach, intestine, colon, rectum, urethra, and vagina. Not to be bound by theory, it is thought that by administering a compound of the invention to a mammal by application or other means to a mucous membrane or the skin of a mammal, is advantageous, for example, due to the presence of specialized and powerful immune cells such as, for example, dendritic cells, e.g., Langerhans cells.

In a particularly preferred embodiment, the present invention contemplates methods, preferably non-invasive, for immunizing a mammal from a specific antigen by transcutaneously administering a conjugate of the invention. One advantage of non-invasive forms of immunization, is that the need for injection of the pharmaceutical composition into the mammal is, at least in part, obviated thus potentially reducing the need for injections and reducing, for example, the mammals' risk of exposure to foreign pathogens, e.g., HIV. The term non-invasive includes methods of administration such as transcutaneous administration through skin and mucous membranes. Examples include, inhalation of the pharmaceutical composition for transcutaneous administration through the mucous membranes of the respiratory tract, swallowing the pharmaceutical composition for administration through, for example, transcutaneous administration, through, for example, the mucous membranes, e.g., of the gastrointestinal tract, e.g., the membranes of the mouth, throat, stomach, intestines, colon and rectum. The invention also pertains to pharmaceutical compositions for the immunization of mammals comprising a toxin-antigen conjugate of the invention and a pharmaceutically acceptable carrier suitable for transcutaneous administration of the conjugate.

In a further embodiment, the invention pertains to pharmaceutical compositions and methods which further comprise adjuvants. An example of an adjuvant is KLH. A critical role in enhancing the ability of compounds to be successfully administered transcutaneously is played by adjuvants (Edelman *Rev. Infec. Dis.* (1980) 2:370-383). Adjuvants have been important in the development of the transcutaneous, e.g., transdermal or mucousal, routes as useful and easily accessible non-invasive methods for administration of compounds to mammals (Snider, *Crit. Rev. Immunol.* (1995) 14:317-348). Suitable adjuvants are well known to those skilled in the relevant arts.

In a further embodiment, the present invention contemplates a method of inducing immunity in a mammal by administering to a mammal a therapeutically effective amount of a toxin-antigen conjugate of the invention and pharmaceutical carrier suitable for administration to the mammal. Preferably, the carrier is suitable for administration nasally, orally, or topically. Advantageously, the method may further comprise the administration of an adjuvant. The invention also pertains to pharmaceutical compositions capable of inducing immunity in a mammal comprising an effective amount of a toxin-antigen conjugate and a pharmaceutical carrier. Preferred carriers include those suitable for administering the conjugate of the invention to the mammal nasally, orally, or topically.

The language "therapeutically effective amount" of the compound is that amount necessary or sufficient to treat or prevent an antigen-related state, e.g. prevent the various morphological and somatic symptoms of an antigen-related state. The effective amount can vary depending on such factors as the size and weight of the subject, the type of illness, or the particular conjugate of the invention. For example, the choice of the conjugate of the invention can affect what constitutes an "effective amount". One of ordinary skill in the art would be able to study the aforementioned factors and make the determination regarding the effective amount of the conjugate of the invention without undue experimentation.

The invention also pertains to a method for presenting antigens on antigen-presenting cells, comprising contacting the antigen-presenting cells with a toxin-antigen conjugate such that the antigen-presenting cells present said antigens. Preferably, the antigens are tumor antigens, e.g., melanoma antigens. It is believed, for example, that the B subunit of verotoxin can stimulate both surface presentation of the antigen by the dendritic cells as well as intracellular antigen processing.

The term "antigen-presenting cells" include those cells which display antigens or antigenic fragments. Examples of antigen-presenting cells include some peripheral blood mononuclear cells and, preferably, dendritic cells, e.g., Langerhans cells In another embodiment, the invention features a pharmaceutical composition which includes a toxin-antigen conjugate and a pharmaceutically acceptable carrier. The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can performs its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present conjugates can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

While it is possible for a compound of the present invention to be administered alone, it is preferable to administer the compound as a pharmaceutical composition. Preferred pharmaceutical compositions include those suitable for administration orally, transdermally, or intrabronchially.

According to the invention, antigens, e.g., Mage 1, either coadministered with a toxin, e.g., the verotoxin B subunit, or coupled, e.g., by covalent linkage, to the toxin are administered to a subject to stimulate the antigen-presenting capabilities of dendritic cells, e.g., Langerhans cells, and act as a vaccine. Such vaccines can be administered orally, transdermally or intrabronchially, and are capable of stimulating dendritic cells in the tissue to which they are exposed.

The invention further pertains to a pharmaceutical composition for treating an antigen-related state in a mammal. The pharmaceutical composition includes an effective amount of a toxin-antigen conjugate and a pharmaceutically acceptable carrier. Preferably, the antigen-related state is a tumor, e.g., melanoma, and the toxin-antigen conjugate comprises, for example, a B subunit of a verotoxin.

The invention also pertains to a vaccine for vaccinating a mammal, e.g., a human, for a antigen-related state, e.g., a tumor, comprising a toxin-antigen conjugate and a pharmaceutically acceptable carrier.

The present invention relates to the use of verotoxin B subunits, and hybrid compositions which include all or part of a verotoxin B subunit, to stimulate immune cells, e.g., to stimulate the antigen-presenting function of immune cells, e.g., to provide an effective vaccination strategy.

In certain embodiments, the B toxin of verotoxin (VT) is administered by administering a holotoxin (e.g., VT1, VT2, VT2c, VT2e) to the subject. However, in a preferred embodiment, the B subunit of verotoxin is administered without the toxic portions of VT holotoxin, thereby avoiding holotoxin toxicity. It is believed that the B subunit of verotoxin can stimulate both surface presentation of antigen by the dendritic cells as well as intracellular antigen processing.

In another embodiment, melanoma-associated peptides linked to the verotoxin B chain or to cholera B chain are administered to the subject as anti-tumor vaccines by stimulating dendritic cells and providing active presentation of such antigens to lymphocytes. In a preferred embodiment, tumor lysates are linked to the verotoxin B chain using techniques such as covalent linkages, e.g., cyanogen bromide activation. In yet another preferred embodiment, adjuvants, e.g., KLH, are co-administered.

This invention is further illustrated by the following examples which should not be construed as limiting. The contents of all references, patent applications, patents, and published patent applications cited throughout this application are hereby incorporated by reference.

EXAMPLE

Major Histocompatibility Complex Class I Presentation of Exogenous Soluble Tumor Antigen Fused to the B Fragment of Shiga Toxin: Shiga Toxin B-Fragment Targets Exogenous Antigen into the MHC Class I Presentation Pathway.

Recombinant proteins composed of the Shiga toxin B. fragment fused to a CD8 epitope derived from the Mage 1 tumor antigen (van der Bruggen, P. et al., *Science* (1991) 254:1643-1647) were constructed. This antigen, initially cloned from human melanoma is expressed in tumors of different origin. No expression of this gene was found on a large panel of normal tissue except for testis which did not express MHC class I molecules (van der Bruggen, P. et al., *Science* (1991) 254:1643-1647). The in vitro ability of this engineered tumor antigen to be processed and presented in a class I restricted pathway was investigated.

Materials and Methods

Cells

Peripheral blood mononuclear cells (PBMC) were separated from peripheral blood of HLA-A1+ healthy donors by centrifugation on Ficoll-Hypaque gradients. The dendritic cells used in the present study were generated from PBMC according to the protocols described previously (Sallusto, F. and Lanzavecchia, A., *J Exp. Med.* (1994) 179:1109-1118). Briefly, adherent cells were obtained after 2 hours incubation of the Ficoll/Hypaque gradient-separated mononuclear population on plastic dishes. These cells were then cultured in RPMI 1640 medium supplemented with 10% heat inactivated Fetal Calf Serum, 2 mM L-Glutamine, 50 IU/ml penicillin, 50 µg/ml streptomycin, 5% sodium pyruvate ("complete medium") and 500 U/ml recombinant GM-CSF (Leucomax, Molgramostin, Sandoz Pharma, Basel, Switzerland) and 100 IU/ml IL4 (Diaclone, Besancon, France). On day 3, GM-CSF and IL4 were added once again and dendritic cells obtained at day 6-7 were used for antigen presentation assays.

The B lymphoblastoid cell line LB 705 (HLA-A1, A2, B8, B27) was previously described (Van der Bruggen, P. et al. *Eur. J. Immunol.* (1994) 24:3038-3043). The EBV-transformed B cell line BM 21 was derived from an homozygous HLA-A1 individual (Yang, S. Y. et al., *Immunobiology of HLA*. (Springer-Verlag, N.Y.: 1989)). The HLA-A2 EBV-transformed B cell line V.1 was a gift of Dr. U. Blank. All the B lymphoblastoid cell lines were maintained in complete medium supplemented with 1 µM2-mercaptoethanol.

MZ2 CTL82/30 and LB373 CTL 246/15 clones recognized respectively the 160-168 peptide of the Mage 1 protein in an HLA-A1 restricted manner (Traversari, C. et al., *J. Exp. Med.* (1992) 176:1453-1457) and the 27-35 peptide of the Mart 1 protein in an HLA-A2 restricted manner (Coulle, P, G. et al., *J. Exp. Med.* (1994) 180:35-42).

Culture of CTL followed the protocols described by Traversari et al. with slight modifications (Traversari, C. et al., *Immunogenetics* (1992) 35:145-152). Briefly, $3 \times 10^5$ CTL were cultured in 2 ml complete Iscove medium containing L-arginine (116 µg/ml), L-asparagine (36 µg/ml) and L-glutamine (216 µg/ml) supplemented with 10% human pool A, B and O serum (SAB) from healthy donors and in the presence of $10^6$ irradiated (100 Gy) LG-2 EBV feeder cells, $10^6$ irradiated (30 Gy) allegoric PBMC, PHA-L (5 µg/ml) and IL-2 (150 IU/ml). Three or four days after stimulation, CTL were diluted in culture medium supplemented with IL-2 (50 IU/ml). Stimulation of CTL with feeder cells was repeated once a week. For IFNγ assays, CTL cultures were used six days after the last restimulation.

Plasmid Constructions and Fusion Peptide Production

The construction of the pSU108 based plasmids expressing the B-fragment of Shiga toxin or fusion proteins in which a N-glycosylation site and an active (KDEL) or inactive (KDELGL) endoplasmic reticulum (ER) retrieval signal were introduced at the C-terminus of the B-fragment, were described previously (Johannes, L. et al., *J. Biol. Chem.* (1997) 272:19554-19561). A PCR based strategy was used to introduce the Mage 1 epitope and its 5' and 3' flanking sequences (DVKEADPTGHSYVLG) into the Not 1 site of previously constructed B-Glyc-KDEL and B-Glyc-KDELGL expression vectors. The resulting fusion proteins were termed B-Mage1-Glyc-KDEL and B-Mage1-Glyc-KDELGL. Sequences were checked by double-stranded DNA sequencing. The proteins were expressed in *E. coli* strain DH5α and purification was essentially done as described (Johannes, L. et al., *J. Biol Chem.* (1997) 272: 19554-19561).

Briefly, after preparation of periplasmic extracts, they were loaded on a QFF column (Pharmacia) and eluted by a linear NaCl gradient (120 to 400 mM) in 20 mM Tris/HCl, pH 7.5. Shiga B-Mage 1 fusion protein containing fractions were dialyzed against 20 mM Tris/HCl, pH 7.5, reloaded on a Mono Q column (Pharmacia), and eluted as before.

The Antennapedia-Mage 1 (Antp-Mage1) fusion gene was obtained by insertion of synthetic oligonucleotides encoding the Mage 1 epitope and its 5' and 3' flanking sequences (see above) between the XhoI and BamH1 restriction sites of the PAH61S plasmid in replacement of the Rab3 coding sequence (Perez, F. et al., *J. Cell. Sci.* (1992) 102:717-722). An NdeI-BamHI restriction fragment containing the Antp-Mage1 sequence was then subcloned into the Novagen plasmid pET 2gb(+) (R&D System, London, UK) in which the fusion protein expression was under the control of T7 promoter and His-tagged at its C-terminus. The fusion peptides were expressed in *E. coli* strain BL21 (DE3)Lys after IPTG induction as described (Studier, F. W. et al., *Methods in Enzymol.* (1990) 185: 60-89). The Antp-Mage1 protein was then purified on Ni-NTA agarose gel (QIAGEN GmbH, Hilden, Germany) under denaturing conditions according to the supplier's protocols. The resulting fusion proteins were estimated to be 95% pure by SDS-polyacrylamide gel electrophoresis and Coomassie blue staining (FIG. 1 A, B, and C).

Western Blot

After high resolution SDS-polyacrylamide gel electrophoresis, proteins were electro-transferred onto a nitrocellulose membrane (BA85, 0.45 mm, Schleicher & Schuell, Darsell Germany) in transfer buffer (192 mM glycine, 25 mM Tris base pH 8.3, 20% ethanol) using the transblot cell (Bio-Rad). The membrane was then saturated for 1 hour at 37° C. in 20 mM Tris (pH 7.4), 150 mM NaCl (Western buffer (WB)), 5% bovine serum albumin (BSA), 0.1% Tween 20 and incubated for 18 hours at 4° C. with either the mouse monoclonal antibody 13C4 (4 µg/ml) (ATCC, Rockville, USA) directed against the B-fragment of Shiga toxin for Shiga B-Mage 1 Fusion proteins or the mouse anti-(His)$_6$-tag antibody (1 µg/ml) (Dianova, Takara Biomedical Europe S.A. Genevilliers, France) for the Antp-Mage1 fusion protein. The membranes were washed with WB and 0.1% Tween 20 and incubated for 1 hour with anti-mouse immunoglobulin coupled to horseradish peroxidase (Amersham, Les Ulis, France). After washing with WB and 0.1% Tween 20, the filters were incubated with the Western-blotting reagent ECL (Amersham), and chemiluminescence was detected by exposure of the membranes to Biomax MR films (Kodak).

Antigenic Peptides

Synthetic peptides 27-35 Mart 1 (AAGIGILTV) and 160-168 Mage 1 (EADPTGMSY) were obtained from Neosystem (Strasbourg, France) and derived from previously published sequences (Traversari, C. et al. *J. Exp. Med.* (1992) 176:1453-1457; Kawakami, Y. et al. *J. Exp. Med.* (1994) 180:347-352).

Antigen Presentation Assays

Antigen presenting cells (PBMC, B-EBV, T cells or dendritic cells) were plated in 96-well flat bottom microplates at $10^5$ cells/well and pulsed at 37° C. for 4 hours or 15 hours with antigen in 100 µl Iscove medium without SAB. At the end of the incubation, the medium was removed and 20,000 CTL clones were added to each well in 100 µl CTL culture medium containing 25 units/ml of IL2. After 24 hours, 50 µl of supernatant were harvested and IFNγ was measured by ELISA (Diaclone, Besancon, France).

In some experiments, the cells were fixed in 1% paraformaldehyde for 10 min at room temperature and extensively washed before transfer to microplates. Where appropriate, Brefeldin A (Sigma) or Chloroquine (Sigma) were added at 2 µg/ml and 250 µM respectively for 30 min prior to addition of antigen and were present during the antigen processing incubation at the same final concentrations.

DTAF Coupling

B-Mage1-Glyc-KDEL was coupled to DTAF (5-(4,6-dichlorotriazin-2-yl)amino)fluorescein) essentially as described previously. Briefly, 60 µg of recombinant B-Mage1-Glyc-KDEL in 20 mM HEPES, pH 7.4, 150 mM NaCl were added to 250 mM NaHCO$_3$ and a 10 fold molar excess of DTAF (Sigma) and incubated by end-over-end rotation for 30 min at room temperature. 0.2 mM NH$_4$Cl was then added and the coupled protein was purified on PD10 columns (Pharmacia).

Internalization and Immunofluorescence Staining $10^5$ B-EBV BM 21 cells, grown on polylysine pretreated 12-mm round glass coverslips, were incubated on ice for 45 min with 1 µg/ml of DTAF-labeled recombinant B-Mage1-Glyc-KDEL. After washing, the cells were incubated for 1 hour at 37° C., fixed with 3% paraformaldehyde for 10 min, permeabilized with saponin (0.01%), stained with the monoclonal anti-Lamp-2 antibody H4B4 (Pharmingen, San Diego) and revealed with a Texas Red coupled anti-mouse IgG antibody (Jackson, West Grove, USA).

Confocal laser scanning microscopy and immunofluorescence analysis were performed using a TCS4D confocal microscope based on a DM microscope interfaced with an argon/krypton laser (Johannes, L. et al., *J. Biol. Chem.* (1997) 272:19554-19561).

Results

Biochemical Characterization of Shiga B-Mage 1 and Antp-Mage 1 Fusion Proteins

As shown in FIG. 1A, Mage 1 containing B-fragment fusion proteins carrying an active ER retrieval signal (the tetrapeptide KDEL) or an inactive version of this signal (the hexapeptide KDELGL) migrate under reducing conditions with molecular weights of about 11.3 kDa corresponding to their expected sizes. Western blot analysis with a monoclonal anti-B-fragment antibody (13C4) confirmed the identity of all purified Shiga B fusion proteins (FIG. 1B).

The two Shiga B-Mage 1 fusion proteins were already, after purification, partially cleaved, yielding 9.5 kDa fragments (FIGS. 1 A-B). It should be noted, however, that the Mage 1 sequence is internal within B-Mage 1-Glyc-KDEL and B-Mage1-Glyc-KDELGL. Thus, even if C-terminal cleavage was responsible for the production of the 9.5 kDa fragments, as judged from their molecular weights, they still contain the Mage 1 epitope.

Another fusion protein was constructed in which the Mage 1 peptide was fused to a polypeptide derived from the third segment of the Antennapedia homeodomain (Perez, F. et al., *J. Cell. Sci.* (1992) 102:717-722). Coomassie blue polyacrylamide gel staining and western blot analysis identified the recombinant Antp-Mage 1 protein as a 15 kDa polypeptide (FIG. 1C).

Figure 2:
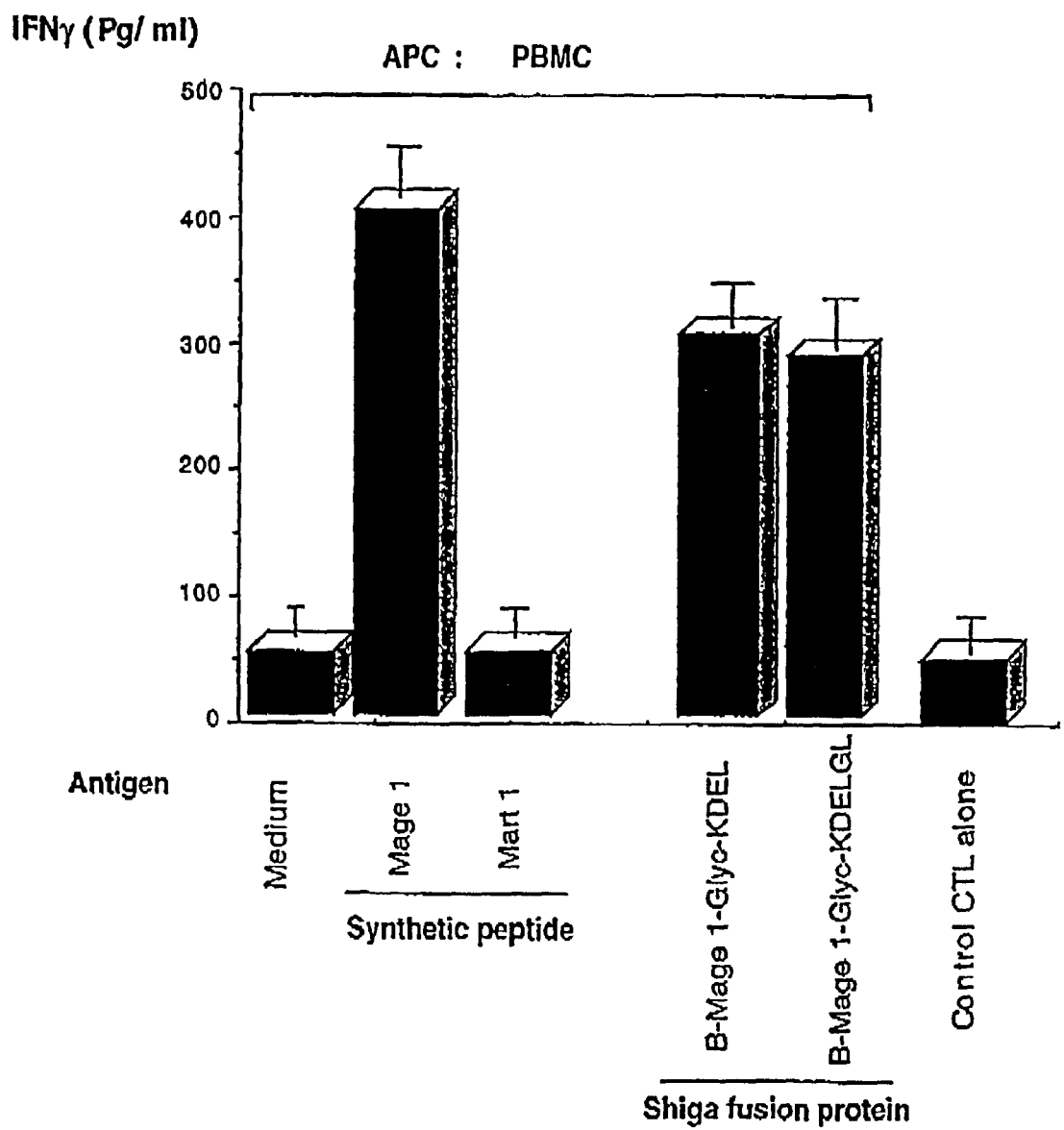
FIG. 2: MHC class 1 presentation of soluble Shiga B-Mage 1 fusion proteins to PBMC: role of KDEL sequence. PBMC ($5 \times 10^4$) were pulsed overnight with either peptide 191 age 1 (1 µM) or Mart 1 (11 µM) or the Shiga B-Mage 1 fusion proteins (1 µM) with active (B-Mage 1-Glyc-KDEL) or inactive (B-Mage1-Glyc-KDELGL) ER retrieval sequence. After washing, $2 \times 10^4$ Mage 1 specific cytotoxic T cells (Clone B2/30) were incubated with the pulsed PBMC for 24 hours. Supernatants were then harvested and tested for IFNγ production. The data are means of triplicate±standard deviation (bars) and are representative of at least two similar experiments.

Presentation of Exogenous Soluble Shiga B-Mage 1 Fusion Proteins by Class I Molecules:
Role of the KDEL Sequence To assess the potential of exogenous Shiga B-Mage 1 fusion protein to drive MHC class I presentation of internal Mage 1 epitope, PBMC were pulsed with B-Mage1-Glyc-KDEL. As shown in FIG. 2, these PBMCs efficiently presented the Mage 1 peptide derived from Shiga B-Mage 1 fusion protein in an HLA-A1 restricted manner to specific CTLs. The influence of the KDEL signal on the efficiency of presentation was then tested. Both the KDEL- and the KDELGL-bearing Shiga B-Mage 1 fusion proteins were able to activate a Mage 1 specific HLA class I restricted CTL response (FIG. 2). Similar activity of the two molecules were also observed when different concentrations of both protein were tested (data not shown). Presence of the PBMC during the experiment was necessary because direct CTL activation by Shiga B-Mage 1 fusion proteins did not occur (data not shown).

For the following examples, only B Mage1-Glyc-KDEL was used since the antigen presentation abilities of KDEL- and KDELGL-bearing Shiga B-Mage 1 fusion proteins were equivalent.

Analysis of MHC Class I Presentation of Soluble BMage1-Glyc-KDEL Protein by Different Antigen Presenting Cells.

Homogeneous antigen presenting cells were sensitized with Shiga B-Mage 1 fusion protein. After pulsing B lymphoblastoid cells and dendritic cells, activation of the class I restricted Mage 1 specific CTL was demonstrated (FIG. 3). These results were observed with two different B-EBV cell lines (EIM21 and LB 705) and dendritic cells derived from two HLA-A1 donors. As low as 0.2 μM of Shiga B-Mage 1 protein was sufficient to sensitize B-EBV cells and dendritic cells for Mage 1 peptide presentation (FIG. 3). Conversely, T cell clones sensitized in vitro with Shiga B-Mage1 fusion protein could not activate autologous T cell clones (FIG. 3). The 82/30 cloned T cells used for this study as antigen presenting cells expressed HLA-A1 molecules and presented synthetic Mage 1 peptide (data not shown).

Analysis of the Specificity of MHC Class I Presentation of Mage 1 Peptide Derived from Exogenous Soluble Shiga B-Mage 1 Fusion Protein by B Lymphoblastoid Cell Lines.

An exogenous class I restricted antigen presentation pathway is rarely observed in B-EBV cells (Rock, K, L., *Immunol. Today* (1996) 17:131-137; Watts, C., *Annu. Rev. Immunol* (1997) 15:821-850). To demonstrate the role of Shiga toxin B-fragment in this process, a recombinant protein was produced in which the B fragment was replaced by the third segment of the antennapedia homeodomain, a transcription factor from Drosophila. This domain has been shown to translocate some peptides into the cytoplasm and the nucleus of eukaryotic cells (Perez, F. et al., *J. Cell. Sci*. (1992) 102:717-722). It also targeted exogenous antigen in the MHC class I processing pathway in some cell types (Schutze-Redelmeier, M. P. et al., *J. Immunol*. (1996) 157:650-655). As shown in FIG. 4A, no presentation of Mage 1 peptide could be detected when the antp-Mage 1 fusion protein was used to pulse HLA-A1 B-EBV cells. When B-EBV cells with HLA-A2 haplotype were sensitized with Shiga B-Mage 1 protein, no activation of Mage 1 specific CTL could be observed (FIG. 4A). The specificity of the activation was also supported by the absence of stimulation of Mart 1 specific CTL clones when HLA-A1 or -A2 B-EBV cells were pulsed with Shiga B-Mage 1 fusion protein (FIG. 4 B). B-Glyc-KDEL without Mage 1 epitope was not recognized by the Mage 1 specific CTL clone (FIG. 4A). Altogether, these data demonstrate a specific HLA-A1 restricted presentation of Mage 1 peptide derived from the Shiga B-Mage 1 fusion protein.

Role of Internalization and Intracellular Processing in the MHC Class I Presentation of Soluble Shiga B-Mage 1 Fusion Protein by B Lymphoblastoid Cell Lines.

The ability of recombinant Shiga B-Mage 1 fusion protein to direct internal peptide epitopes into the class I restricted pathway and its dependence on the internalization of this protein was tested.

Paraformaldehyde fixed B lymphoblastoid cells did not allow presentation of Shiga B-Mage 1 derived Mage 1 peptide to class 1 restricted Mage 1 specific CTL clone, whereas exogenous synthetic Mage 1 peptide incubated with fixed B-ESBV cells activated this CTL (FIG. 5A). This precluded extracellular Shiga B-Mage 1 processing as an explanation for the observed exogenous HLA class I restricted antigen presentation. To further demonstrate that intracellular transport or processing were involved in this model of antigen presentation, Brefeldin A (BFA) which blocks protein transport in the biosynthetic/secretory pathway, or Chloroquine which raises the pH of endosomes and thus inhibits endosomal proteolysis were used. Neither chloroquine nor BFA interfered with presentation of exogenous synthetic Mage 1 peptide (FIG. 5B). The antigen presenting ability of these cells was maintained. In contrast, the presence of BFA during the incubation of soluble Shiga B-Mage 1 fusion protein prevented the presentation of the Mage 1 T cell epitope (FIG. 5C). This effect was not observed with chloroquine. In control experiments, the same concentration of chloroquine was efficient to inhibit HLA class II restricted presentation of tetanus toxin derived peptides (data not shown).

Internalization of Shiga B-Mage 1 Fusion Protein in B-EBV Cells: Analysis of its Colocalization with a Lysosomal Marker.

To follow the intracellular transport of B-Mage 1-Glyc-KDEL in B-EBV cells, the protein was covalently linked to the fluorophore DTAF. After its binding to cells on ice and subsequent incubation for 1 hour at 37° C., the protein was internalized into cytoplasmic structures with a marked juxtanuclear staining (FIG. 6A). The staining patterns corresponded to the Golgi and ER compartments, consistent with the previous studies on HeLa cells (Johannes, L. et al., *J. Biol Chem*. (1997) 272:19554-19561). Using an antibody against the lysosomal associated membrane protein-2 (Lamp-2) (FIG. 6B) in double labeling immunofluorescence experiment, the Shiga B-Mage 1 fusion protein was largely excluded from Lamp-2 positive lysosomal compartments (FIG. 6C).

Approximately 10-20% of the B-EBV cells showed intermediate to strong B-fragment specific staining after B-Mage-Glyc-KDEL internalization. Such heterogeneity between cells of a given population has already been described (Sandvig, K. et al. *J. Cell Biol*. (1994) 126:53-64) and is due to variations in the toxin receptor expression in function of the cell cycle (Pudymaitis, A. and Lingwood, C. A., *J. Cell. Physiol.* (1992) 150:632-639).

Discussion

Figure 3:
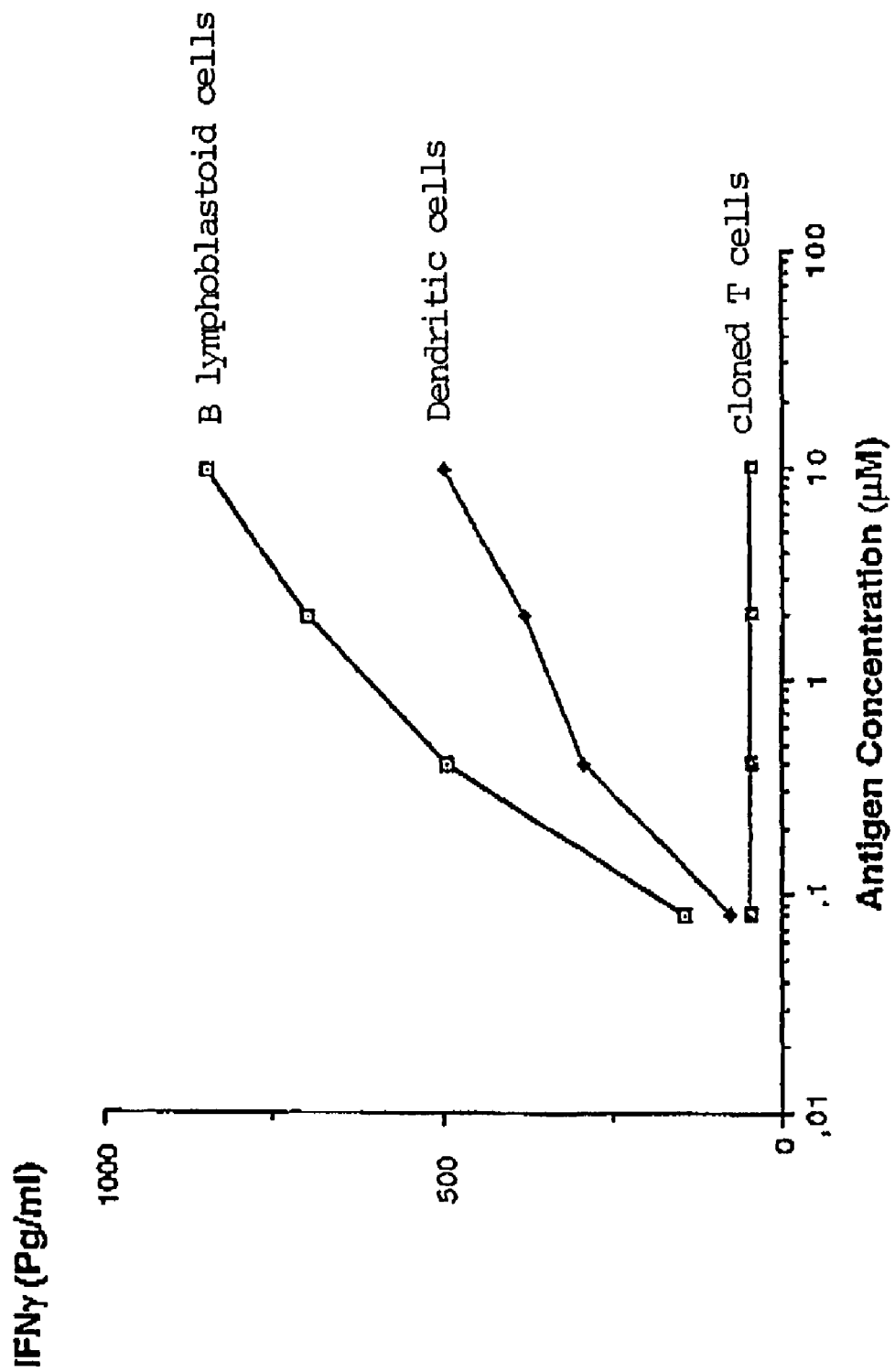
FIG. 3: MHC class 1 presentation of soluble Shiga B-Mage 1 fusion protein by different kinds of Antigen Presenting Cells. B Lymphoblastoid cells, dendritic cells, and cloned T cells were pulsed as described in FIG. 2 with soluble Shiga B-Mage 1 fusion protein. Peptide Mage 1 presentation was tested with the 82/30 CTL.
Figure 4:
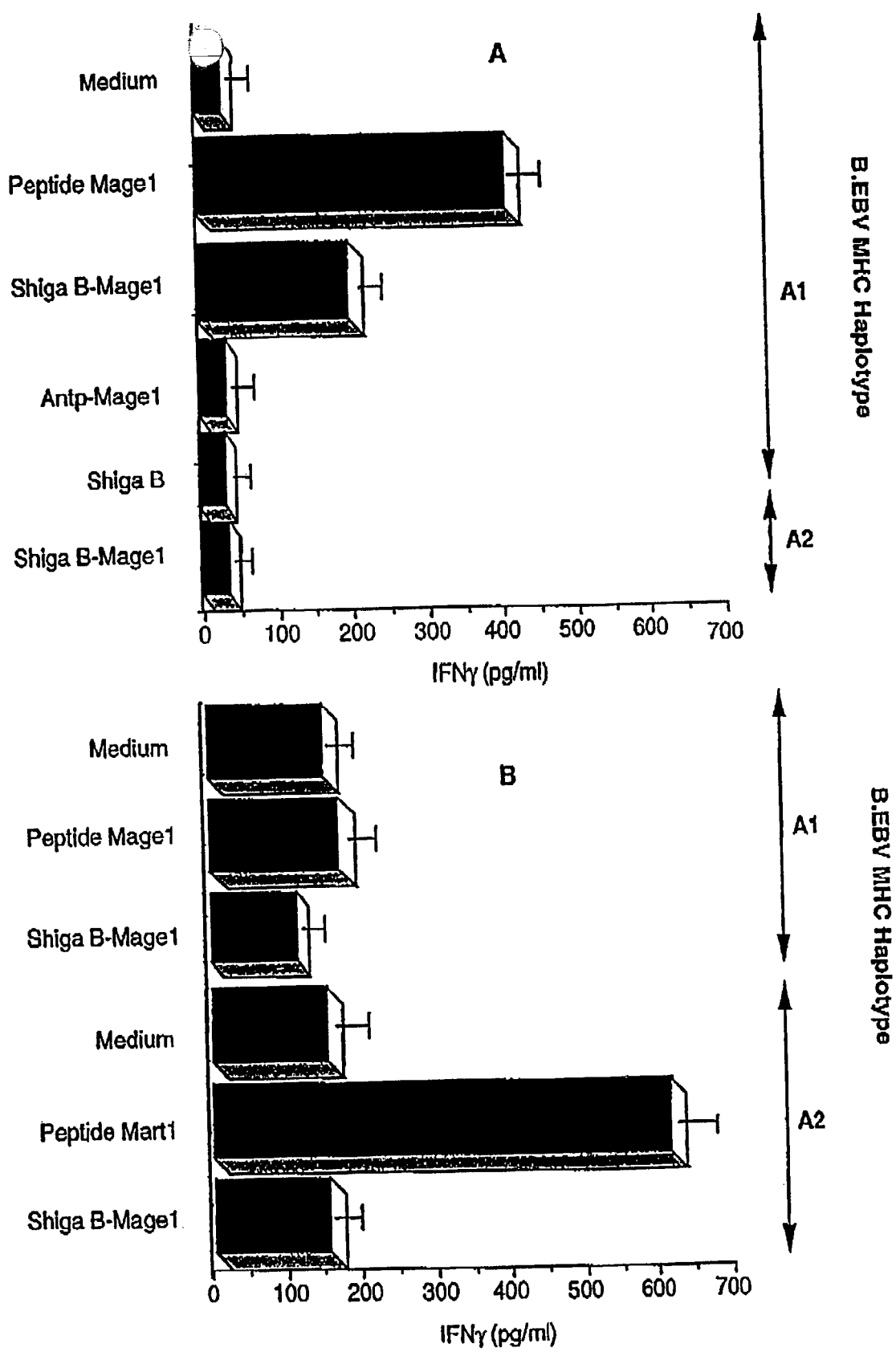
FIG. 4: Analysis of the specificity of M1 IC class I presentation of soluble Shiga B-Mage 1 fusion protein by B lymphoblastoid cell lines. The B lymphoblastoid cell lines BM21 (HLA-A1) or B-V.1 (HLA-42) were pulsed overnight with medium alone, synthetic peptide Mage 1 (1 μM), the synthetic peptide Mart 1 (1 μM), the Shiga B-Mage 1 fusion protein (1 μM), the recombinant Antp-Mage 1 fusion protein, and the wild type Shiga toxin B-fragment. After washing, Mage 1 specific CTL 82/30 (A) or Mart 1 specific LB 373 CTL (B) were incubated with the pulsed B-EBV for 24 hours. Supernatants were then harvested and tested for IFNγ production. The data are means of triplicate±standard deviation (bars) and are representative of at least two similar experiments.
Figure 5:
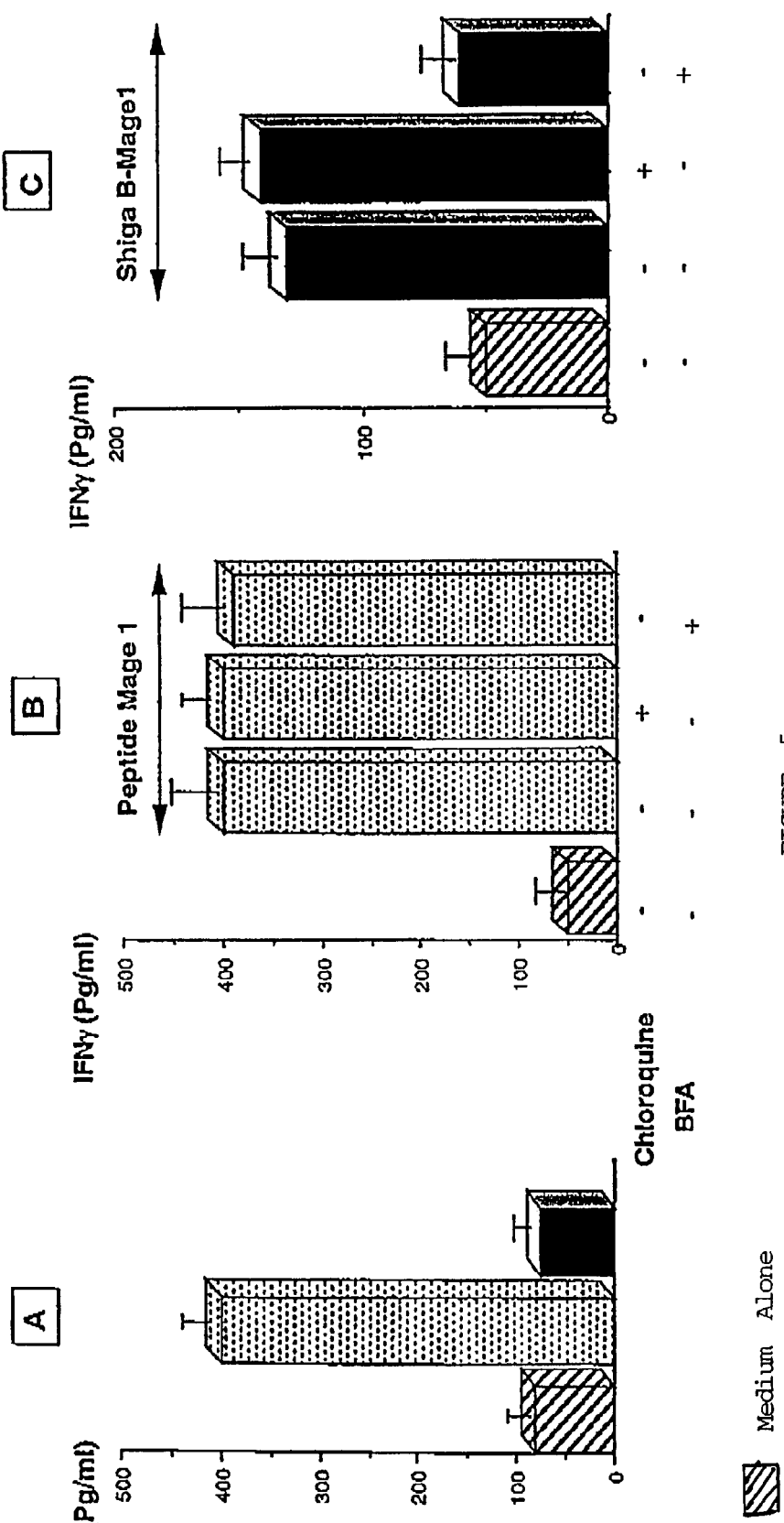
FIG. 5: MHC class I presentation of soluble Shiga B-Mage 1 fusion protein by B lymphoblastoid cell lines. Pole of internalization (A) and intracellular processing (B-C: A: Paraformaldehyde fixed B lymphoblastoid cell line (BM21) was pulsed overnight with synthetic Mage 1 peptide (1 μM), Shiga B-Mage 1 fusion protein (1 μM) or medium alone. After washing, Mage 1 specific CTL were incubated with the pulsed B-EBV for 24 hours. Supernatants were then harvested and tested for IFNγ production. B and C: Some unfixed B-EBV (BM21) were pretreated chloroquine (250 μM) or Brefeldin A (2 μg/ml) for 30 min before they were pulsed for 4 hours with synthetic Mage 1 peptide (1 μM) or Shiga B-Mage 1 fusion protein (1 μM) or medium alone. After washing, Mage 1 specific CTL were incubated with the pulsed B-EBV for 24 hours. Supernatants were then harvested and tested for IFNγ production. The data are means of triplicate±standard deviation (bars) and are representative of at least two similar experiments.
Figure 6:
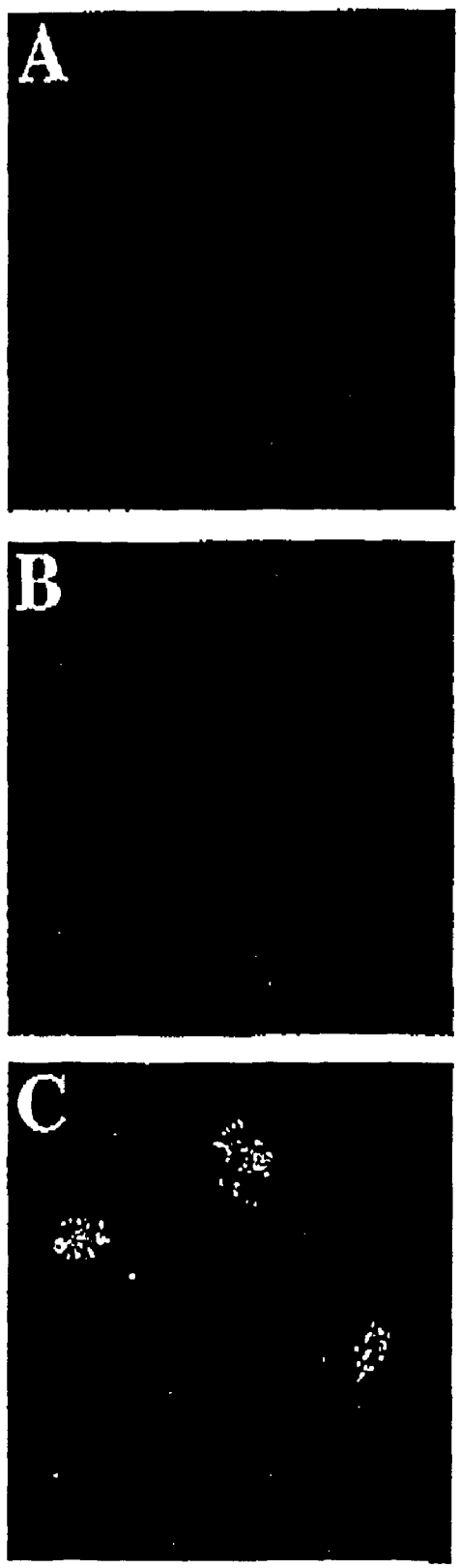
FIG. 6. Analysis of Shiga B-Mage 1 fusion protein localization after internalization into B-EBV cells. B-EBV cells were incubated with DTAF-labeled B-Mage 1-Glyc-KDEL (A) on ice for 45 min, washed and left for 1 hour at 37° C. Cells were then fixed with paraformaldehyde, permeabilized with saponin and stained with a monoclonal anti-lamp-2 antibody (B). In C, B-fragment specific labeling (A) and Lamp-2 labeling (B) are superimposed. Representative images obtained by confocal microscopy are shown.

It has been demonstrated that a soluble CD8 tumor antigen fused to the B fragment of Shiga toxin is efficiently presented in an HLA class I restricted manner to specific CTL. Although some partial proteolytic cleavage of the purified recombinant protein was observed, extracellular processing is unlikely for the following reasons: i) the CTL Mage1 epitope is internal within the Shiga B-Mage 1 fusion protein and therefore it requires two or more separate and specific cleavage events to generate HLA-A1 binding Mage 1 peptide; ii) the absence of presentation of Mage 1 peptides derived from Shiga B-Mage 1 fusion protein by T cells which in the same experiment kept the ability to bind and present synthetic Mage 1 peptides discounts extracellular cleavage (FIG. 3); iii) paraformaldehyde fixed antigen presenting cells were able to present synthetic exogenous Mage 1 peptides, yet they did not process Shiga B-Mage 1 fusion proteins; and iv) Brefeldin A prevented the presentation of Mage 1 epitope derived from soluble Shiga B-Mage 1 protein. Since Brefeldin A inhibits both the transport of Shiga B-Mage 1 to the endoplasmic reticulum (Johannes, L. et al., *J. Biol. Chem.* (1997) 272: 19554-19561) and the association and transport of processed peptides with nascent class I molecules to the plasma membrane (Monaco, J. J., *Immunol. Today* (1992) 13:173-179), its exact mechanism of inhibition remains to be established. However, the experiments with BFA indicate that internalization of Shiga B-Mage 1 fusion protein is required for efficient HLA-class I restricted presentation.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for stimulating an immune response in a mammal, comprising administering to said mammal through a mucous membrane a Shiga toxin-antigen conjugate and an adjuvant such that an immune response in said mammal is stimulated, wherein said toxin-antigen conjugate is associated through a non-covalent interaction or covalently linked, wherein an antigen in said toxin-antigen conjugate is an antigen from cancer cells, and wherein said antigen in said Shiga toxin-antigen conjugate is introduced into a major histocompatibility complex (MHC) class I pathway and wherein said immune response involves stimulation of dendritic cells, wherein said dendritic cells include Langerhans cells.

2. The method of claim 1, wherein said mucous membrane is located in the respiratory tract, gastrointestinal tract or reproductive tract of said mammal.

3. The method of claim 2, wherein said mucous membrane of the respiratory tract is selected from the mucous membranes of said mammal's nose, throat or lungs.

4. The method of claim 2, wherein said mucous membrane of the gastrointestinal tract is selected from mucous membranes of said mammal's mouth, throat, stomach, small intestine, large intestine, colon, urethra or rectum.

5. The method of claim 1, wherein said Shiga toxin-antigen conjugate comprises a cancerous breast tumor antigen.

6. The method of claim 5, wherein said cancerous breast tumor antigen is from a cancerous breast tumor lysate.

7. The method of claim 6, wherein said cancerous breast tumor antigen is from breast tissue.

8. The method of claim 1, wherein said Shiga toxin in said Shiga toxin-antigen conjugate is produced recombinantly.

9. The method of claim 1, wherein said non-covalent interaction is a protein-protein interaction, a hydrophobic interaction, a Van der Waals interaction, or an ionic interaction.

10. The method of claim 1, wherein said Shiga toxin-antigen conjugate further comprises an active or inactive endoplasmic reticulum retrieval signal.

11. The method of claim 1, wherein said mammal is a human.

12. The method of claim 1, wherein said Shiga toxin-antigen conjugate is administered to said mammal nasally or orally.

13. A method for treating a cancerous tumor in a mammal comprising administering to said mammal through a mucous membrane an effective amount of a Shiga toxin-antigen conjugate and an adjuvant, stimulating an immune response in said mammal, thereby treating said cancerous tumor in said mammal, wherein said Shiga toxin-antigen is associated through a non-covalent interaction or covalently linked, and wherein said antigen in said Shiga toxin-antigen conjugate is introduced into a major histocompatibility complex (MHC) class I pathway and wherein said immune response involves stimulation of dendritic cells, wherein said dendritic cells include Langerhans cells.

14. The method of claim 13, wherein said mucous membrane is located in the respiratory tract, gastrointestinal tract or reproductive tract.

15. The method of claim 13, wherein said cancerous tumor is a breast tumor.

16. The method of claim 13, wherein said mammal is a human.

17. The method of claim 13, wherein said mammal is suffering from said cancerous tumor.

18. The method of claim 13, wherein said Shiga toxin-antigen conjugate is administered nasally or orally.

19. A method for stimulating an immune response in a mammal, comprising administering to a mammal through a mucous membrane a Shiga toxin B-antigen conjugate and an adjuvant such that an immune response in said mammal is stimulated, wherein a Shiga toxin B fragment is fused to an antigen to form said conjugate, wherein said antigen in said Shiga toxin B-antigen conjugate is introduced into a major histocompatibility complex (MHC) class I pathway and wherein said immune response involves stimulation of dendritic cells, wherein said dendritic cells include Langerhans cells.

20. The method according to claim 19, wherein said Shiga toxin B fragment is produced recombinantly.

21. A method for stimulating an immune response in a mammal, comprising administering to said mammal intranasally a Shiga toxin-antigen conjugate and an adjuvant such that an immune response in said mammal is stimulated, wherein said toxin-antigen conjugate is associated through a non-covalent interaction or covalently linked, wherein an antigen in said toxin-antigen conjugate is an antigen from cancer cells, and wherein said antigen in said Shiga toxin-antigen conjugate is introduced into a major histocompatibility complex (MHC) class I pathway and wherein said immune response involves stimulation of dendritic cells, wherein said dendritic cells include Langerhans cells.

* * * * *

UNITED STATES PATENT AND TRADEMARK OFFICE
CERTIFICATE OF CORRECTION

| | | |
|---|---|---|
| PATENT NO. | : 8,367,071 B2 | Page 1 of 1 |
| APPLICATION NO. | : 10/368314 | |
| DATED | : February 5, 2013 | |
| INVENTOR(S) | : Green | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 843 days.

Signed and Sealed this
Eighteenth Day of November, 2014

Michelle K. Lee
*Deputy Director of the United States Patent and Trademark Office*